United States Patent
Orgal (10) Patent No.: US 9,381,397 B2
(45) Date of Patent: Jul. 5, 2016

(54) COMPUTER-AIDED PHYSIOTHERAPEUTIC STAIR AND GAIT SYSTEM

(71) Applicant: DPE Medical Ltd, Shoeva (IL)

(72) Inventor: Daniel Orgal, Shoeva (IL)

(73) Assignee: DPE MEDICAL LTD, Shoeva (IL)

( * ) Notice: Subject to any disclaimer, the term of this patent is extended or adjusted under 35 U.S.C. 154(b) by 419 days.

(21) Appl. No.: 14/084,639

(22) Filed: Nov. 20, 2013

(65) Prior Publication Data

US 2015/0141201 A1 May 21, 2015

(51) Int. Cl.
*A63B 23/04* (2006.01)
*A63B 24/00* (2006.01)
*A63B 22/04* (2006.01)

(52) U.S. Cl.
CPC ......... *A63B 23/0405* (2013.01); *A63B 24/0087* (2013.01); *A63B 22/04* (2013.01); *A63B 23/0458* (2013.01)

(58) Field of Classification Search
CPC .. A63B 23/045; A63B 24/0087; A63B 22/04; A63B 23/0458; A63B 12/0464; E04F 11/04; E04F 11/1041
See application file for complete search history.

(56) References Cited

U.S. PATENT DOCUMENTS

| | | | | |
|---|---|---|---|---|
| 3,497,215 | A * | 2/1970 | Harrison | A63B 21/154 482/53 |
| 3,743,283 | A * | 7/1973 | Garrett | A63B 23/0458 108/166 |
| 5,328,420 | A * | 7/1994 | Allen | A63B 22/04 482/37 |
| 5,507,708 | A * | 4/1996 | Ma | A63B 23/0458 482/52 |
| 5,556,352 | A * | 9/1996 | Chang | A63B 22/04 482/51 |
| 5,584,779 | A * | 12/1996 | Knecht | A63B 24/00 434/250 |
| 5,769,759 | A * | 6/1998 | Alter | A63B 22/04 482/37 |
| 5,833,576 | A * | 11/1998 | Henmi | A63B 23/0458 482/52 |
| 5,901,813 | A * | 5/1999 | Orgal | B66B 9/08 187/200 |
| 5,907,935 | A * | 6/1999 | Elena | E04F 11/035 256/65.15 |
| 5,980,429 | A * | 11/1999 | Nashner | A61B 5/1036 434/247 |
| 6,238,320 | B1 * | 5/2001 | Flanagan | A63B 3/00 482/130 |
| 6,402,664 | B1 * | 6/2002 | Marston | A63B 23/0458 482/51 |
| 6,474,024 | B1 * | 11/2002 | Macintyre | E04H 3/126 52/10 |
| 6,601,677 | B1 * | 8/2003 | Storm | B66B 9/0869 187/200 |
| 7,104,901 | B1 * | 9/2006 | Mason | A63B 5/16 473/446 |
| 7,383,600 | B2 * | 6/2008 | Carrigan | E01D 15/24 14/69.5 |
| 8,091,294 | B2 * | 1/2012 | Whalen | A01K 1/035 52/182 |
| 8,807,283 | B2 * | 8/2014 | Shell | B66B 9/0869 182/1 |
| 9,091,083 | B1 * | 7/2015 | Goudreau | E04F 11/066 |
| 2006/0199703 | A1 * | 9/2006 | Shifferaw | A63B 23/0458 482/52 |
| 2007/0004567 | A1 * | 1/2007 | Shetty | A61H 3/008 482/69 |
| 2009/0124464 | A1 * | 5/2009 | Kastelic | A63B 17/04 482/52 |
| 2010/0099541 | A1 * | 4/2010 | Patel | A63B 21/00181 482/52 |
| 2012/0052013 | A1 * | 3/2012 | Chapman | A01K 15/027 424/9.2 |

* cited by examiner

*Primary Examiner* — Sandhara Ganesan
(74) *Attorney, Agent, or Firm* — Mark M. Friedman (57) ABSTRACT

A computer-aided physiotherapeutic stair & gait system has a set of at least three horizontal tread surfaces and an associated drive system for adjusting a rise height between adjacent of the tread surfaces to form a set of stairs with uniform pitch for a range of different rise heights. A sensor set measures parameters related to physiotherapy performed using the set of stairs and provides an output to a computer system. The sensors include one or more of: a rise height sensor for sensing the pitch of the stairs, a heart rate sensor, a handrail grip position sensor, and load cells for analyzing the distribution of the weight of a patient during use of the system.

21 Claims, 8 Drawing Sheets

COMPUTER-AIDED PHYSIOTHERAPEUTIC STAIR AND GAIT SYSTEM

FIELD AND BACKGROUND OF THE INVENTION

The present invention relates to physiotherapy devices and, in particular, it concerns a physiotherapeutic stair system in which treatment is enhanced and/or documented by use of a computer system associated with an integrated sensor set.

Many patients require physiological rehabilitation for various reasons. These include, for example, victims of traffic accidents, patients who have suffered from a cardiac episode or underwent a cardiac medical procedure, as well as individuals that have had a cerebral episode, invasive medical procedures, or sustained injuries of violence and the like. These patients need to receive physiotherapeutic treatment in rehabilitation wards of various institutions or by professional physiotherapists, for the purpose of a gradual return to regular life.

The practicing of walking, ascending and descending stairs is a central part of the rehabilitation process. The ability to ascend and descend stairs is a vital component in the assessment process performed by the medical staff when deciding whether a patient can be discharged from the rehabilitative institution to his or her home.

One example of a suitable device for practicing ascending and descending of stairs is described in U.S. Pat. No. 5,901,813, and is commercially available from DPE Medical Ltd. (Israel) under the name Dynamic Stair Trainer (DST). The device consists of number of stairs whose height can be altered simultaneously according to the need and ability of the current patient.

Stair trainers used in physiotherapy for ascending and descending stairs are preferably static during use with a uniform pitch, simulating the look and feel of conventional stairs. It is also preferable that adjustment of the height occurs through a purely vertical motion without changing the depth of the tread surface of each step, and that the steps have closed riser surfaces without overlap between steps to minimize risk of tripping.

Existing step trainers of this type do not provide integrated tools to facilitate analysis and assessment of progress in stair-mobility treatment.

There is therefore a need for a physiotherapeutic stair system in which treatment would be enhanced and/or documented by use of a computer system associated with an integrated sensor set.

SUMMARY OF THE INVENTION

The present invention is a physiotherapeutic stair system in which treatment is enhanced and/or documented by use of a computer system associated with an integrated sensor set.

According to the teachings of an embodiment of the present invention there is provided, a system comprising: (a) a set of at least three horizontal tread surfaces; (b) a drive system mechanically linked to the set of tread surfaces and configured to displace at least two of the tread surfaces vertically so as to adjust a rise height between adjacent of the tread surfaces in such a manner as to form a set of stairs with uniform pitch for a range of different rise heights; (c) a sensor set comprising at least one sensor deployed for measuring a parameter related to physiotherapy performed using the set of stairs; and (d) a computer system comprising at least one processor and a non-volatile data storage medium, the computer system being associated with the sensor set so as to receive the at least one parameter.

According to a further feature of an embodiment of the present invention, the at least one sensor comprises a sensor deployed to measure a parameter indicative of a current rise height between adjacent of the tread surfaces.

According to a further feature of an embodiment of the present invention, the computer system comprises a user interface configured to receive an input indicative of the identity of a patient undergoing treatment, and wherein the computer system stores records of a plurality of treatment sessions for each patient, the records including the current rise height.

According to a further feature of an embodiment of the present invention, the computer system is configured to generate a stair-capability measure for the patient, the stair-capability measure being indicative of a current ability of the patient to climb stairs and a rate of improvement of the current ability.

According to a further feature of an embodiment of the present invention, the at least one sensor comprises at least one heart rate sensor deployed to measure a parameter indicative of a heart rate of a patient on the set of stairs.

According to a further feature of an embodiment of the present invention, the system further comprises a handrail extending along at least one side of the set of stairs, and wherein the at least one heart rate sensor is integrated into the handrail.

According to a further feature of an embodiment of the present invention, the system further comprises a handrail extending along at least one side of the set of stairs, and wherein the at least one sensor comprises at least one contact sensor deployed to generate an output indicative of a location at which a patient using the set of stairs is holding the handrail.

According to a further feature of an embodiment of the present invention, the at least one sensor comprises at least one load cell deployed to measure a load applied to each of the tread surfaces.

According to a further feature of an embodiment of the present invention, the computer system is configured to: (a) monitor a sum of the loads measured by the plurality of load cells; and (b) determine a current weight of a patient on the set of stairs.

According to a further feature of an embodiment of the present invention, the system further comprises a handrail extending along at least one side of the set of stairs, and wherein the computer system is further configured to subtract a current sum of the loads from the current weight to determine a current patient load on the handrail.

According to a further feature of an embodiment of the present invention, the computer system is further configured to generate a warning signal if the current patient load on the handrail exceeds a predefined percentage of the current weight of the patient.

According to a further feature of an embodiment of the present invention, the computer system is configured to process signals from the load cells to determine at least one measure of gross motor skill control during stair usage.

According to a further feature of an embodiment of the present invention, the computer system is configured to process signals from the load cells to determine a time period taken by a patient to move from one of the tread surfaces to another of the tread surfaces.

According to a further feature of an embodiment of the present invention, the at least one load cell is implemented as at least two load cells deployed so as to generate signals allowing determination of a loading position relative to a length of each of the tread surfaces.

According to a further feature of an embodiment of the present invention, the computer system is configured to determine, for each stair transition by a patient, whether the patient has lead with a right leg or a left leg, and to generate an indication of bilateral or unilateral usage.

According to a further feature of an embodiment of the present invention, the at least one load cell is implemented as a set of load cells deployed so as to generate signals allowing determination of a loading position in two dimensions for each of the tread surfaces.

According to a further feature of an embodiment of the present invention, the computer system is configured to generate a warning signal when loading of a tread surface satisfies conditions identifying excess front-edge loading of the tread surface.

According to a further feature of an embodiment of the present invention, the computer system is functionally interconnected with the drive system, the computer system being configured to retrieve from the data storage medium or from remote data storage data relating to at least one past treatment session for a given patient, the computer system being configured to actuate the drive system to bring the set of stairs to an initial rise height for a next treatment session, the initial rise height being derived at least in part from the data.

According to a further feature of an embodiment of the present invention, the drive system is configured to displace the tread surfaces so as to form the set of stairs with a plurality of rise heights substantially spanning a majority of a range from 0 cm to 18 cm.

According to a further feature of an embodiment of the present invention, the drive system is further configured to displace the tread surfaces so that all of the plurality of tread surfaces are juxtaposed as a continuous flat surface.

According to a further feature of an embodiment of the present invention, the drive system is configured to displace the tread surfaces in a purely vertical motion, and wherein a plurality of the tread surfaces each has an associated vertical riser surface.

According to a further feature of an embodiment of the present invention, the computer system further comprises communication components for connection to a wired or wireless network, and wherein the computer system is configured to transfer via the network a report containing data relating to treatment sessions of a patient.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a physiotherapeutic stair system in which treatment is enhanced and/or documented by use of a computer system associated with an integrated sensor set, and corresponding methods for managing and/or assessing treatment using such a device.

The principles and operation of stair systems according to the present invention may be better understood with reference to the drawings and the accompanying description.

Referring now to the drawings, FIGS. 1-6 show various full or partial views of a physiotherapeutic stair training system, generally designated 10, constructed and operative according to a particularly preferred embodiment of the present invention.

Mechanical Structure

The structural basis of system 10 according to this particularly preferred example closely parallels the implementation of the aforementioned Dynamic Stair Trainer (DST) commercially available from DPE Medical Ltd. (Israel). The device has a set 12 of at least three, and in the case shown here four, horizontal tread surfaces, individually referred to as TR0, TR1, TR2 and TR3. A drive system 14 is mechanically linked to the set 12 of tread surfaces and configured to displace at least two of the tread surfaces TR1-TR3 vertically so as to adjust a rise height between adjacent of the tread surfaces in such a manner as to form a set of stairs 12 with uniform pitch for a range of different rise heights.

Figure 4:
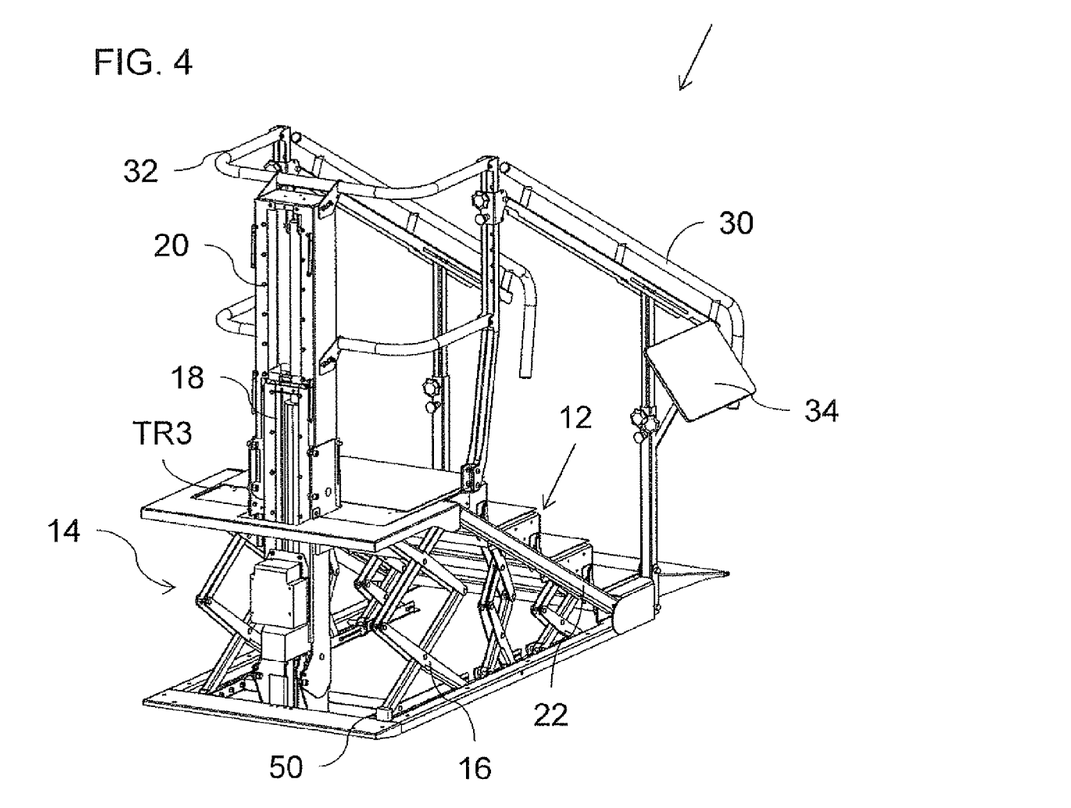
FIG. 4 is a rear isometric view of the physiotherapeutic stair system of FIG. 1 deployed to the maximum height, with rear covers removed to reveal components of a drive system.

A preferred but non-limiting implementation of drive system 14 is best seen in FIG. 4. Under each tread surface is a scissors mechanism 16, preferably doubled so as to support each side of the tread surface, which allows vertical movement of the tread surface while ensuring that it remains parallel to the floor. A linear drive, shown here in the form of a screw actuator 18, is deployed in a column 20 at the back of the top tread surface TR3 and deployed to move tread surface TR3 vertically. Other types of actuators, such as hydraulic or pneumatic actuators, may also be used. Two side rails 22 are pivotally linked to top tread surface TR3 so as to be lifted at one end as the top tread surface rises. Each of the other tread surfaces has lateral projections 24 (see FIG. 5) which engage rails 22 as a track, thereby lifting each tread surface in proportion to the elevation of the top surface and maintaining a set of stairs 12 of uniform pitch.

Parenthetically, it will be noted that the drawings show the system of the present invention with various covers and a protective skirt removed to reveal various components of the mechanism.

It is important for stair therapy treatment that the steps are closed steps, i.e., with closed riser surfaces, so that the toes of a patient do not get caught beneath the step. To this end, each tread surface (other than TR0) is generally integrally formed with a riser surface 26 to form a step structure. Drive system 14 is preferably configured to displace the tread surfaces in a purely vertical motion, such as through the aforementioned scissors mechanisms 16.

Figure 1:
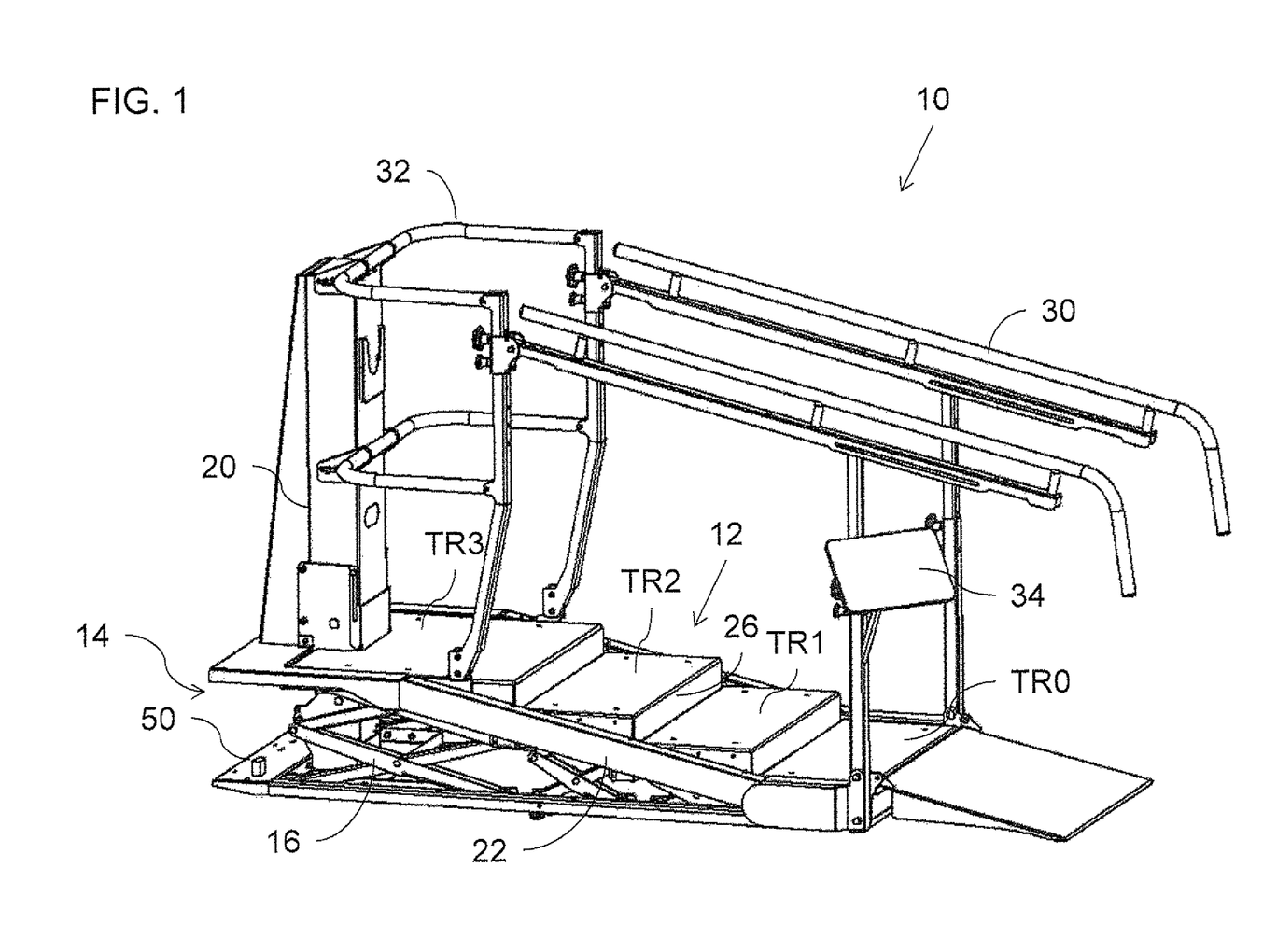
FIG. 1 is an isometric view of a physiotherapeutic stair system, constructed and operative according to an embodiment of the present invention, showing the system deployed to an intermediate rise height.
Figure 2:
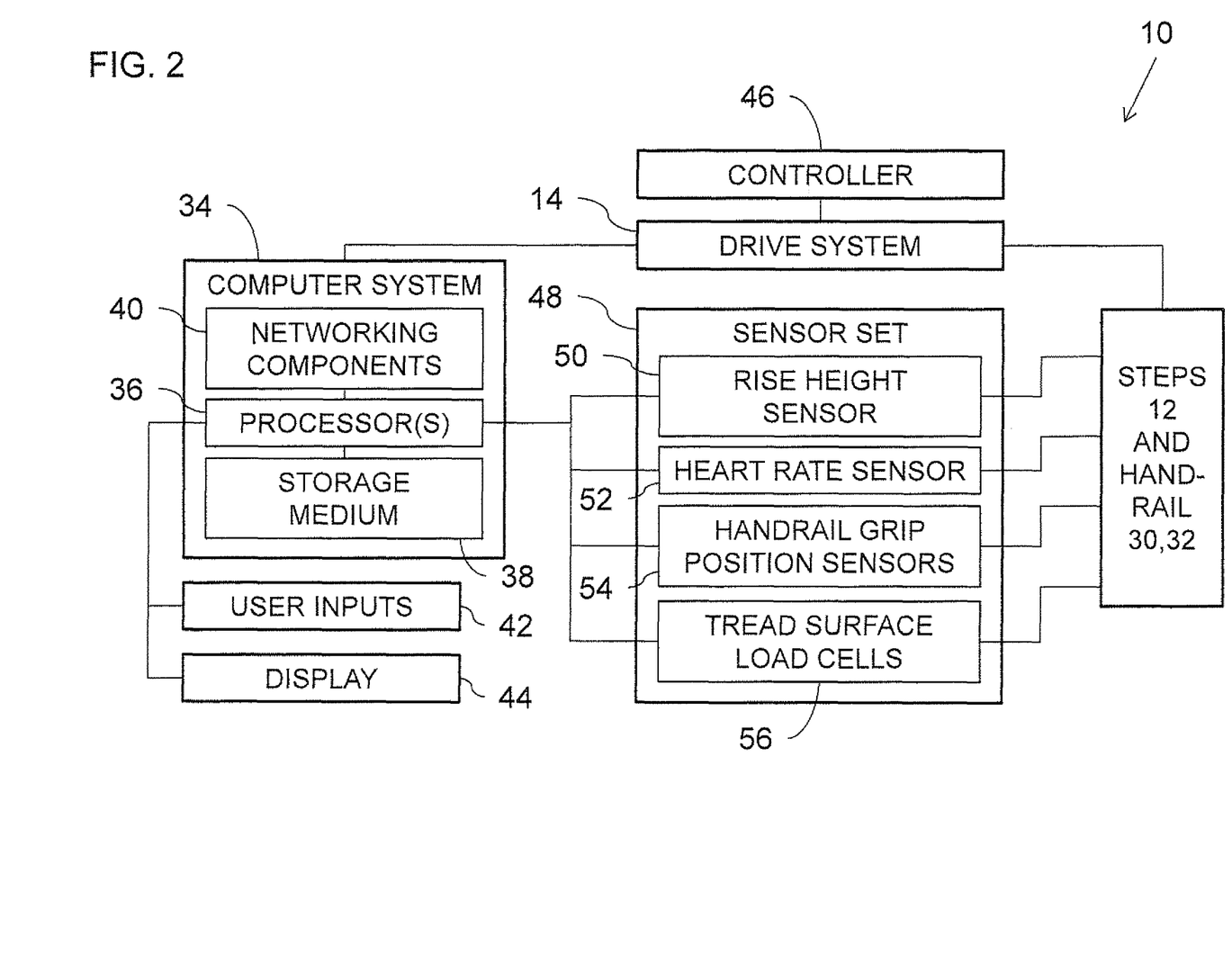
FIG. 2 is a block diagram of the physiotherapeutic stair system of FIG. 1.
Figure 3A:
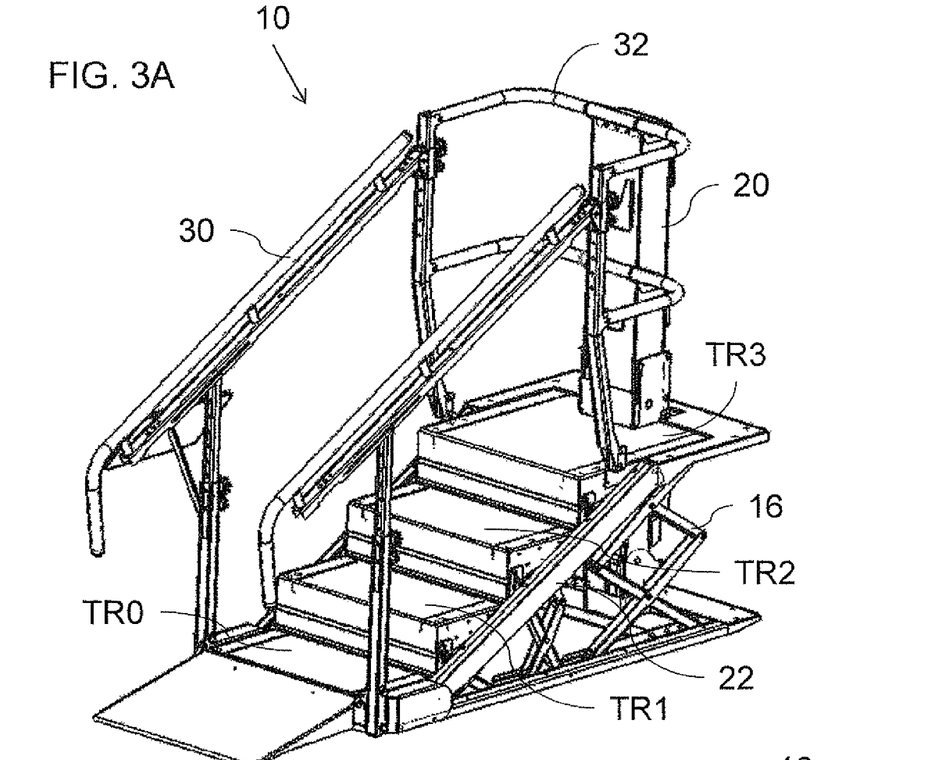
FIGS. 3A and 3B are isometric views of the physiotherapeutic stair system of FIG. 1 showing the system deployed, respectively, to a maximum rise height and a zero rise height, useful for ambulatory therapy between parallel bars.
Figure 5:
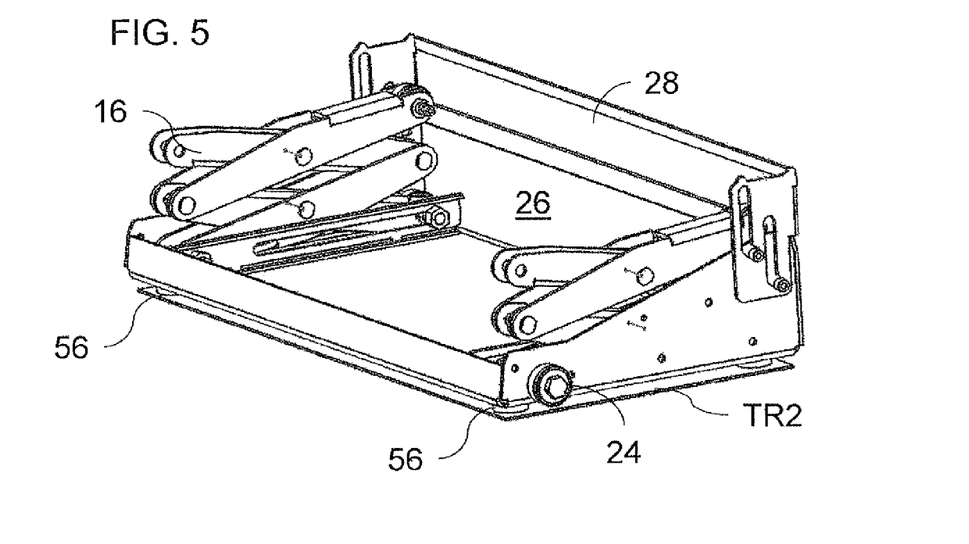
FIG. 5 is an enlarged isometric view of a step unit from the physiotherapeutic stair system of FIG. 1.
Figure 6:
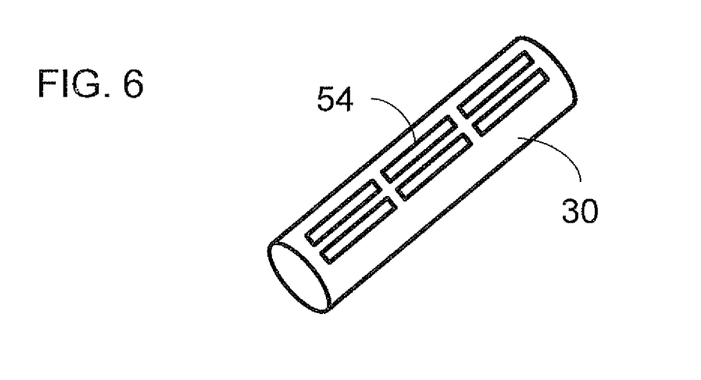
FIG. 6 is a schematic isometric view of a section of a handrail from the physiotherapeutic stair system of FIG. 1, illustrating a preferred deployment of sensing elements.

In the particularly preferred case illustrated in FIG. 5, each step also includes a telescopic extension portion 28 which provides an extension to riser surface 26 in the higher raised positions of the system, such as is seen in FIG. 3A. The use of a telescopic extension portion allows the system to assume a fully lowered state (FIG. 3B) in which a spacing from the floor is less than the maximum rise height of the set of stairs 12 in the fully raised state.

The system preferably also includes at least one handrail extending alongside the set of stairs 12. In the implementation illustrated here, an adjustable-height handrail 30 is provided on each side of the set of stairs 12, and is complemented by a handrail portion 32 extending around the top tread surface, which is here extended to form an upper platform to facilitate turning around between the ascent and descent. The handrail may additionally or alternatively be adjustable in horizontal position, to allow adjustment of the spacing between the right and left rails.

Drive system 14 is preferably configured to displace the tread surfaces so as to form the set of stairs 12 with a plurality of rise heights substantially spanning a majority of a range from 0 cm to 18 cm. "Substantially spanning" in this context refers to adjustability which provides either continuous adjustment or a plurality of discrete positions which are spaced apart by no more than 2 cm, and more typically in steps of 1 cm or less. In a particularly preferred implementation, the system provides adjustment to substantially span the entirety of a range of at least 0-18 cm, thereby facilitating practice of all common step sizes.

Figure 3B:
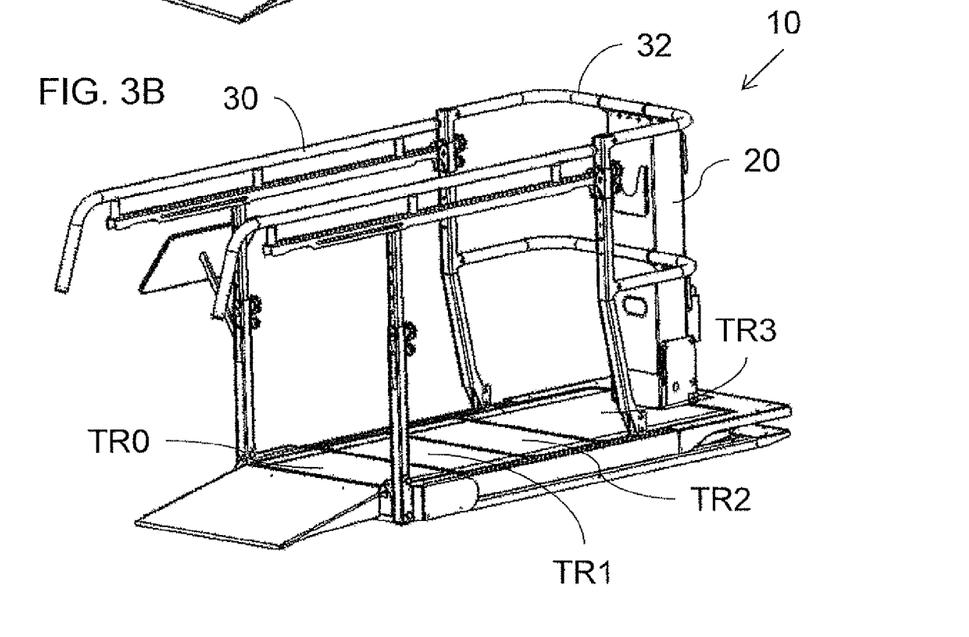

The system preferably assumes a fully flattened (zero step) state, as illustrated in FIG. 3B. In this stage, the plurality of tread surfaces are juxtaposed as a continuous flat surface, which is useful for ambulatory parallel bars therapy.

In addition to the aforementioned components, the present invention features a computer system 34 comprising at least one processor 36 and a non-volatile data storage medium 38, typically together with networking components 40 for connection to a wired or wireless network. Computer system 34 may be any type of suitable computer, including but not limited to, a general purpose computer running suitable software under a suitable operating system, and a dedicated computer system configured by suitable hardware, software and/or firmware to perform the various functions required. In some implementations, computer system 34 may be implemented using a mobile electronics device such as a smartphone operating suitable software and in wireless communication with the various other components of the system.

Computer system 34 is preferably associated with, and possibly integrated with, one or more user input device 42 and a display 44. In one preferred case, the entire computer system 34 is integrated in a "tablet" configuration with a touch-screen which serves as both the input device and the display, as illustrated schematically in FIG. 1.

Control of the up/down motion of drive system 14 may be achieved by pressing directly on up/down buttons on a controller 46 associated with drive system 14. Additionally, or alternatively, control of drive system 14 may be achieved via the user interface of computer system 34.

Computer system 34 is associated with a sensor set 48 including at least one sensor deployed for measuring a parameter related to physiotherapy performed using the set of stairs 12. Preferred examples of the sensors, and corresponding modes of operation of the system, are described below.

Sensor Set

Sensor set 48 may include a wide range of sensors for sensing a variety of parameters related to physiotherapy performed using the set of stairs 12. These parameters may relate to the current state of the set of stairs themselves or to the manner in which a patient is using the set of stairs. Each of the sensors described below is of utility when used alone. Certain particularly preferred implementations include multiple types of sensor, and may combine the data from the various sensors to derive additional information. The particular sensors described herein are exemplary, and are not an exhaustive list.

In certain embodiments, the present invention provides a sensor 50 deployed to measure a parameter indicative of a current rise height between adjacent of the tread surfaces. Sensor 50 may take various forms, including but not limited to: a laser or other rangefinder deployed to measure a distance between the top platform TR3 and the base of the system; an optical or magnetic encoder associated with the screw drive mechanism to count revolutions of the drive; and an angle encoder associated with a mechanical component of one of the scissors mechanisms. This output, after correction of any offset and dividing by the number of steps, provides a direct indication of the current pitch of the set of stairs 12.

In certain embodiments, the present invention provides at least one heart rate sensor 52 deployed to measure a parameter indicative of a heart rate of a patient on the set of stairs 12, before, during and/or after ascending or descending the stairs. According to one preferred implementation, the heart rate sensing is performed via electrodes located on handrails 30 and/or 32 using technology commonly available and implemented in hand grips of many treadmills and other aerobic exercise devices. This technology is well known, and will not be described here in detail. In certain cases, electrodes for heart rate monitoring may be provided only at the positions corresponding to a bottom step grip and a top step grip, for detecting the heart rate prior to and after ascending or descending.

According to a further feature of certain preferred embodiments of the present invention, at least one contact sensor 54 is deployed to generate an output indicative of a location at which a patient using the set of stairs 12 is holding the handrail. The handrail grip position sensors are typically implemented as a series of capacitive or conductive sensors spaced along the handrail, allowing the supporting circuitry to determine where along the handrail the user is currently gripping, as illustrated schematically in FIG. 6. Particularly in the case of conductive sensors, the grip position sensors may advantageously be integrated with heart rate sensing via the same conductive electrodes.

According to a further feature of certain preferred embodiments of the present invention, at least one load cell 56 is deployed to measure a load applied to each of the tread surfaces. In the particularly preferred example of FIG. 5, the upper plate of each tread surface is supported by four load cells, one in each corner, which provides stability and allows detailed analysis of real-time weight distribution over the surface of the tread surface. Similar structures are known in the field of children's games, and are described in the literature such as, for example, in U.S. Pat. No. 8,100,770 to Yarnazaki et al.

Operation

The various sensors of sensor set 48 in conjunction with computer system 34 provide a range of functionality for recording treatment sessions, enhancing and/or rendering safer the treatment itself, and analyzing patient progress, which were not heretofore available in the context of physiotherapeutic stair training or rehabilitation.

For example, the computer system preferably keeps track of patient treatment sessions, either in local data storage or via network access to a remote database, storing records of at least the patient identity as entered or selected via user input 42, the dates of previous treatment sessions, and the maximum rise height achieved in each session. The rise height is preferably derived directly by the system from rise height sensor 50, optionally additionally with input from the load cells 56 to verify that the patient successfully negotiated the stairs at that height. This data allows accurate evaluation of the patient's ability and rate of progress in managing stairs.

This data is preferably used as a basis for computer system 34 to generate a stair-capability measure for the patient, also referred to as a "Stair Factor of Progress" or SFP. The stair-capability measure is indicative of a current ability of the patient to climb stairs and a rate of improvement of the current ability. This may, for example, consist of a number corresponding to the highest rise height in centimeters which the patient is currently able to negotiate plus a letter indicating the rate of progress (corresponding to a range of gradients of a rise-height vs. date graph), such that for example "a" indicates rapid progress or full capability with the range of rise heights considered, "b" indicates a moderate rate of progress, and "c" indicates slow or negligible progress. Thus, for example, a SFP of (4-a) would indicate a current limitation to 4 cm steps, but a rapid rate of improvement whereas (8-c) would indicate a capability of managing 8 cm steps but with expectations that progress beyond that point is currently slow. This SFP will be a standardized parameter which is preferably generated automatically by system 10, and will greatly facilitate communication between medical staff regarding patient capabilities and progress. This stair-capability measure and/or other data relating to an individual therapy session or an entire sequence of treatment sessions can be forwarded to a medical professional or other authorized recipient by computer system 34 via a network.

An additional preferred feature of system 10 is the automatic adjustment of the set of stairs to the correct initial rise height for the beginning of a physiotherapy session. Specifically, computer system 34 is preferably configured to retrieve from data storage medium 38 or from remote data storage, data relating to at least one past treatment session for a given patient, the computer system being configured to actuate drive system 14 to bring the set of stairs 12 to an initial rise height for a next treatment session, the initial rise height being derived at least in part from the data relating to the past treatment. For example, therapy sessions may be begin with steps of 5 cm smaller rise height than the maximum reached in the previous session, and will therefore automatically bring the steps to the appropriate height once a new therapy session for that user is selected.

Turning now to FIGS. 7A-12B, there are shown a range of applications which employ outputs from load cells 56. Although described primarily in the context of stair training, it will be appreciated that most of the functions described below are also applicable to gait therapy implemented when the system is at zero rise height, functioning as an ambulatory parallel-bars system.

Figure 7A:
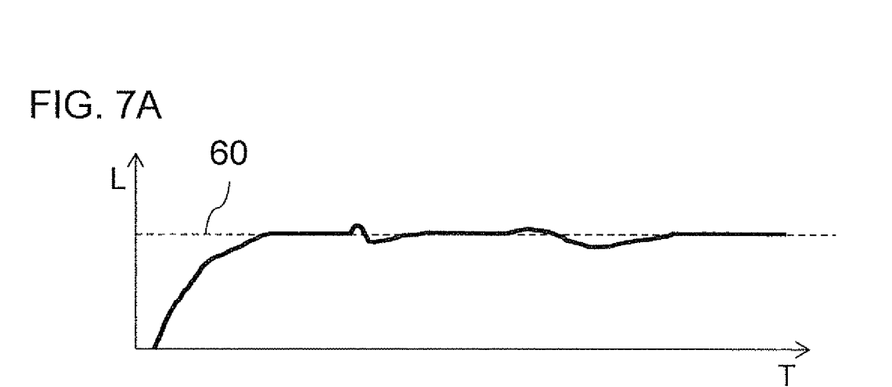
FIGS. 7A and 7B are schematic graphs illustrating variation of a total load on the physiotherapeutic stair system of FIG. 1 with time under normal usage and in a case of excessive load applied to a handrail, respectively.
Figure 7B:
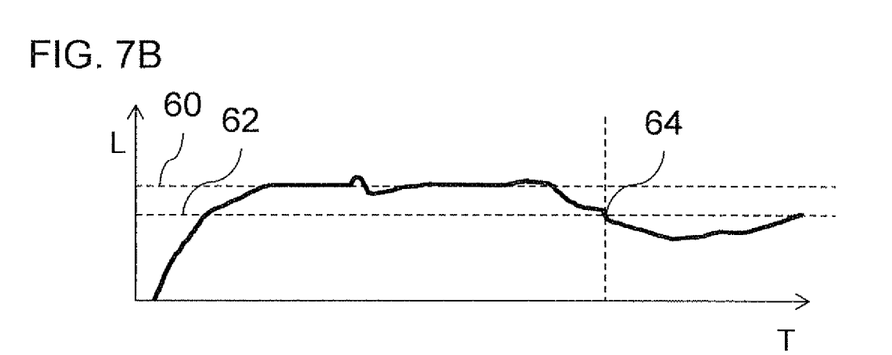

Referring first to FIGS. 7A and 7B, it will be appreciated that by summing the loads applied to the tread surfaces, it is possible to generate a measure of the total load applied to the set of stairs, and thus to determine a current weight of a patient on the set of stairs. FIGS. 7A and 7B illustrate variations of this total load with time during use of the system. It will be noted that the weight is not constant since it undergoes perturbations (due to slight vertical accelerations) as the patient's feet are moved from step to step and the body ascends or descends, as well as through weight transferred to the handrail. However, the variation of total load with time typically exhibits a clear modal value (i.e., the most frequently occurring value) which defines a baseline about which the perturbations occur. The modal value is illustrated in FIG. 7A by a dashed line 60. This value can readily be picked out by computer system 34 via simple processing techniques, and is preferably then used to provide additional functionality.

By way of example, once the current weight of the patient has been determined, computer system 34 is preferably configured to subtract a current sum of the loads from this current weight to determine a current patient load on the handrail. Optionally, a safety limit can be set, for example at a predefined percentage (e.g., 15%) of the current weight, and computer system 34 may be configured to generate a warning signal, for example to an audible buzzer, if the current patient load on the handrail exceeds that predefined percentage of the current weight of the patient. In FIG. 7B, the warning level is represented by dashed line 62 and point 64 represents an incident in which the weight on the handrail has exceeded the allowed limit (shown here as a corresponding decrease in the total measured load), resulting in generation of an alarm.

Figure 8:
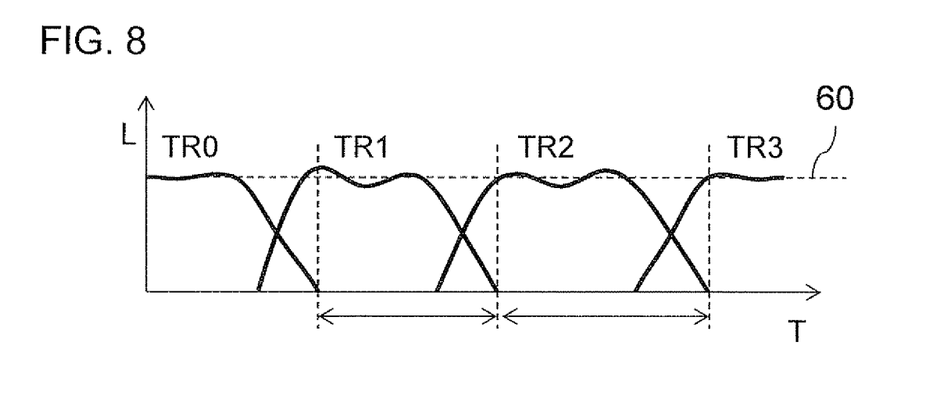
FIG. 8 is a schematic graph illustrating variation of a load on each successive tread surface during use of the physiotherapeutic stair system of FIG. 1.
Figure 9A:
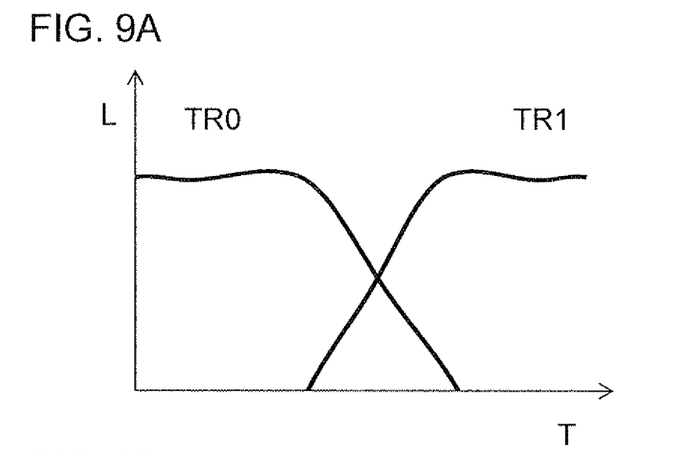
FIGS. 9A and 9B are enlarged views of a region of the graph of FIG. 8 for cases of patients with normal stability and poor stability, respectively.
Figure 9B:
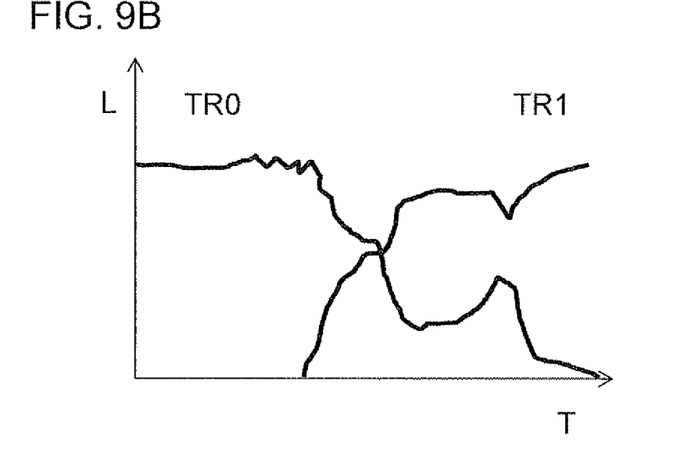

Turning now to FIGS. 8, 9A and 9B, these illustrate separately the load measured on each tread surface, each curve being labeled with the corresponding tread surface label: TR0, TR1, TR2 and TR3. Analysis of these curves and the timing of transferring load between the tread surfaces provides significant information about the ability of the patient to negotiate stairs.

For example, referring to FIG. 8, computer system 34 is preferably configured to process signals from load cells 56 to determine a time period taken by a patient to climb the set of stairs, optionally calculated as a time-per-step or steps-per-minute rate. The time for negotiating each step transfer can be variously defined. In the illustration shown here, the foot-lift from the previous step is taken as the standard reference point from which step transfer duration is measured.

In addition to speed, the form of the load cell signal output can also be used to provide valuable information about the strength and stability of the patient's motion, indicative of their gross motor skill control during stair usage. Thus, in the enlarged views of FIGS. 9A and 9B, the smooth signals of FIG. 9A is indicative of well controlled continuous movements, whereas the unsteady signals of FIG. 9B are indicative of lack of muscle control and/or problems of instability during motion. Computer system 34 is preferably configured to process signals from load cells 56 to determine at least one measure of gross motor skill control during stair usage. In a simple implementation, this may be a measure of the "smoothness" of the signals, determined by the relative weights of low- and high-frequency components in a Fourier transform of the signal. Other forms of processing, such as identifying reversal of the direction of weight transfer between steps, may also provide valuable additional or alternative information.

The data represented by plots such as FIG. 8 may also be used to advantage with output of grip position sensors 54, identifying whether the grip position is within a normal range of positions relative to the current center of gravity of the patient's weight on the tread surfaces. This allows the system to identify whether the patient is reaching ahead to drag himself or herself up to the next step, in contrast to a normal usage of the handrail just for stabilization.

It will be noted that the various functions described thus far can be implemented using a single load cell deployed to support each step. Particularly preferred implementations in which two, or more preferably four, load cells support each step allow for additional functionality, as will now be discussed.

FIGS. 10A-11B illustrate additional functionality which is available when the deployment of load cells allows determination of a loading position relative to a length of each of the tread surfaces, i.e., whether the load is central, to the right or to the left of the step. This can be achieved either by use of two load cells, one supporting each end of the step, or by use of four load cells, by summing the outputs of the right-hand and left-hand sides of each step.

Figure 10A:
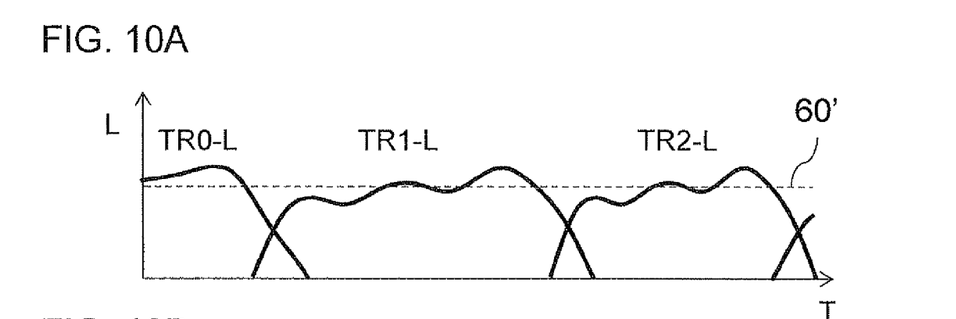
FIGS. 10A and 10B are schematic graphs similar to FIG. 8 but resolved into load applied to the left side and the right side of each tread surface, respectively, for a case of a patient leading repeatedly with the right foot.
Figure 10B:
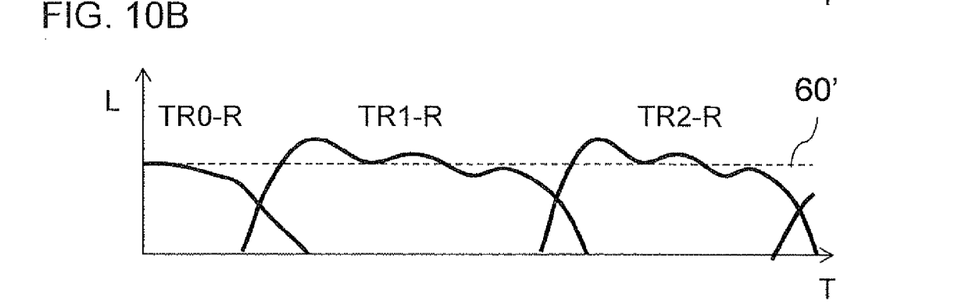

FIGS. 10A and 10B illustrate plots of load on successive steps against time, similar to that of FIG. 8, but where the load on each step is resolved into separate measures of the load on the left side of the step (FIG. 10A) and the load on the right side of the step (FIG. 10B). The dashed line 60' here corresponds to 50% of the current patient weight, which is the load that would be expected if the patient were to be standing on a single step with his or her weight evenly distributed along the length of the step between right and left.

Using this data, computer system 34 is preferably configured to determine, for each stair transition by a patient, whether the patient has lead with a right leg or a left leg, and to generate an indication of bilateral or unilateral usage. Thus, in the example of FIGS. 10A and 10B, the plot for load variation against time for each step shows an initial bias towards the right side, and a final bias prior to lifting of the foot towards the left side. This is indicative (during ascent) of the patient repeatedly leading with the right foot. During descent, when the patient is facing in the opposite direction, the polarity is reversed.

Figure 11A:
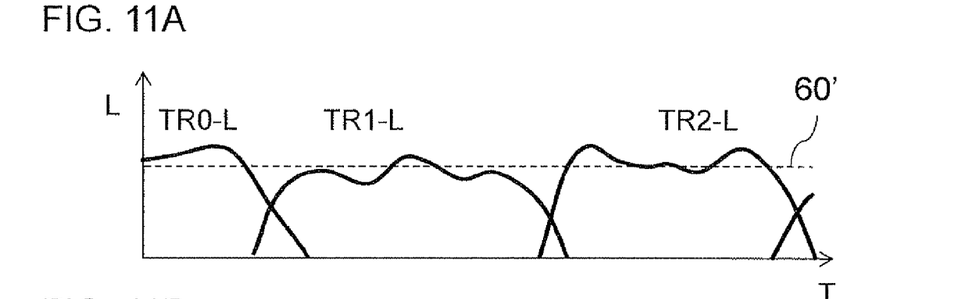
FIGS. 11A and 11B are schematic graphs similar to FIGS. 10A and 10B, respectively, for a patient leading bilaterally.
Figure 11B:
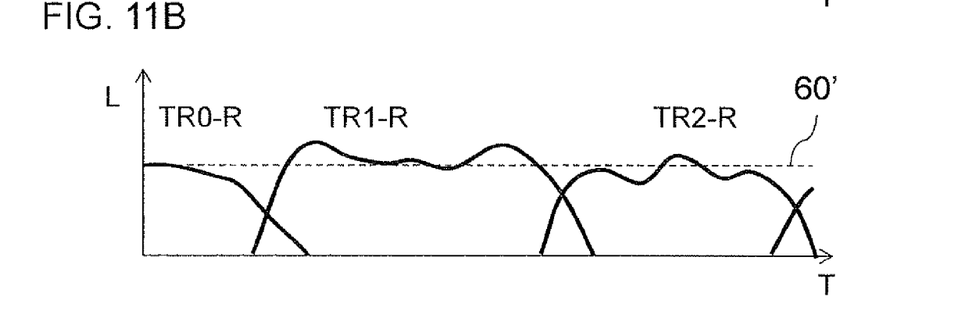

FIGS. 11A and 11B are a further example of a similar pair of plots, this time indicating initial and final bias on tread surface TR1 to the right side, and initial and final bias on tread surface TR2 to the left side. This is indicative of leading with alternate feet.

It will be noted that the average of right-left loading is not necessarily in the middle of the step, and that the modal value of loading for the plots of FIGS. 10A-11B will not necessarily lie on line 60'. An offset from right-left balance is indicative of the patient holding his or her body closer to one handrail than the other. This information is also useful to record. The foot with which the user is leading can still readily be determined by the relative shifts of loading to the right and left, even where there is a consistent trend to one side.

Figure 12A:
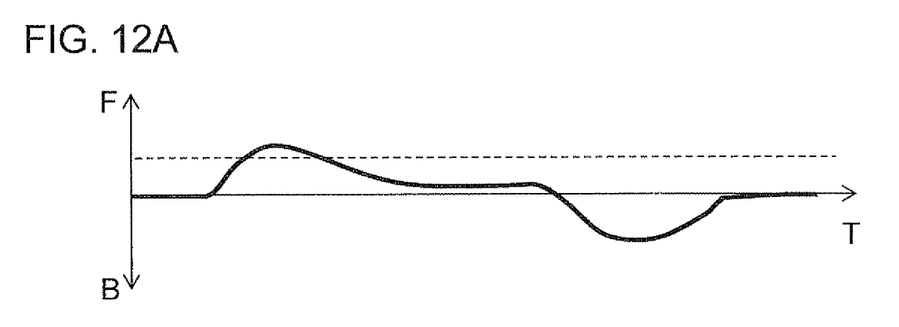
FIGS. 12A and 12B are schematic graphs illustrating a front-back loading balance for a given tread surface under conditions of normal usage and dangerous foot positioning on the edge of a step, respectively.
Figure 12B:
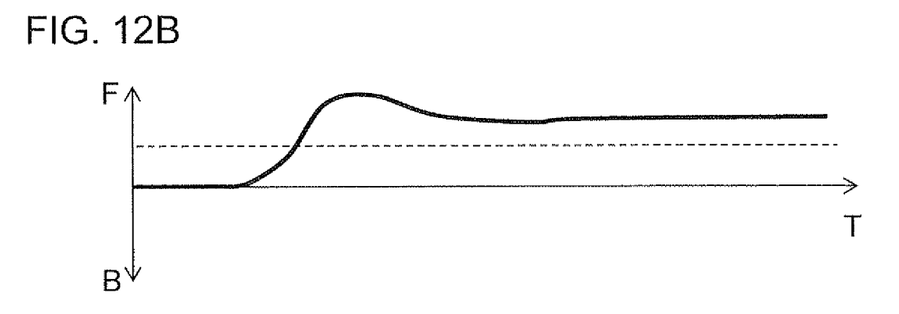

Turning finally to FIGS. 12A and 12B, in the case of an arrangement of three or more non-collinear load cells supporting each tread surface, the set of load cells for each tread surface preferably generate signals allowing determination of a loading position in two dimensions for each of the tread surfaces. This allows assessment of the foot position relative to the front and back edges of the step, and particularly, allows identification of potentially dangerous scenarios in which a patient is transferring their load to a foot which is overlapping the front edge of a step. For this purpose, computer system 34 is preferably configured to generate a warning signal when loading of a tread surface satisfies conditions identifying excess front-edge loading of the tread surface. FIGS. 12A and 12B illustrate a position of the center of loading for a given step along the front-back direction as a function of time. FIG. 12A shows a normal variation. The weight may initially be biased momentarily towards the front of the step, for example as the patient's heal is planted on the step, and may move heavily to the rear of the step as the toe pushes off last. A transient frontal bias on the step is thus not considered problematic.

FIG. 12B illustrates a case in which the frontal bias of the weight remains above a threshold value for an extended period, indicative of a dangerously positioned foot. In this case, the system would preferably generate a warning, typically by sounding a buzzer or other audible alert.

It will be appreciated that the above descriptions are intended only to serve as examples, and that many other embodiments are possible within the scope of the present invention as defined in the appended claims.

What is claimed is:

1. A system comprising:
  (a) a set of at least three horizontal tread surfaces;
  (b) a drive system mechanically linked to said set of tread surfaces and configured to displace at least two of said tread surfaces vertically so as to adjust a rise height between adjacent of said tread surfaces in such a manner as to form a set of stairs with uniform pitch for a range of different rise heights;
  (c) a sensor set comprising at least one sensor deployed for measuring a parameter related to physiotherapy performed using said set of stairs; and
  (d) a computer system comprising at least one processor and a non-volatile data storage medium, said computer system being associated with said sensor set so as to receive said at least one parameter, wherein said at least one sensor comprises a sensor deployed to measure a parameter indicative of a current rise height between adjacent of said tread surfaces.

2. The system of claim 1, wherein said computer system comprises a user interface configured to receive an input indicative of the identity of a patient undergoing treatment, and wherein said computer system stores records of a plurality of treatment sessions for each patient, said records including said current rise height.

3. The system of claim 2, wherein said computer system is configured to generate a stair-capability measure for the patient, the stair-capability measure being indicative of a current ability of the patient to climb stairs and a rate of improvement of the current ability.

4. The system of claim 1, wherein said at least one sensor comprises at least one heart rate sensor deployed to measure a parameter indicative of a heart rate of a patient on said set of stairs.

5. The system of claim 4, wherein the system further comprises a handrail extending along at least one side of said set of stairs, and wherein said at least one heart rate sensor is integrated into said handrail.

6. The system of claim 1, wherein the system further comprises a handrail extending along at least one side of said set of stairs, and wherein said at least one sensor comprises at least one contact sensor deployed to generate an output indicative of a location at which a patient using said set of stairs is holding said handrail.

7. The system of claim 1, wherein said at least one sensor comprises at least one load cell deployed to measure a load applied to each of said tread surfaces.

8. The system claim 7, wherein said computer system is configured to:
(a) monitor a sum of the loads measured by said plurality of load cells; and
(b) determine a current weight of a patient on said set of stairs.

9. The system of claim 7, wherein said computer system is configured to process signals from said load cells to determine at least one measure of gross motor skill control during stair usage.

10. The system of claim 7, wherein said at least one load cell is implemented as at least two load cells deployed so as to generate signals allowing determination of a loading position relative to a length of each of said tread surfaces.

11. The system of claim 7, wherein said at least one load cell is implemented as a set of load cells deployed so as to generate signals allowing determination of a loading position in two dimensions for each of said tread surfaces.

12. The system of claim 11, wherein said computer system is configured to generate a warning signal when loading of a tread surface satisfies conditions identifying excess front-edge loading of said tread surface.

13. The system of claim 1, wherein said computer system is functionally interconnected with said drive system, said computer system being configured to retrieve from said data storage medium or from remote data storage data relating to at least one past treatment session for a given patient, said computer system being configured to actuate said drive system to bring said set of stairs to an initial rise height for a next treatment session, said initial rise height being derived at least in part from said data.

14. The system of claim 1, wherein said drive system is configured to displace said tread surfaces so as to form said set of stairs with a plurality of rise heights substantially spanning a majority of a range from 0 cm to 18 cm.

15. The system of claim 1, wherein said drive system is further configured to displace said tread surfaces so that all of said plurality of tread surfaces are juxtaposed as a continuous flat surface.

16. The system of claim 1, wherein said drive system is configured to displace said tread surfaces in a purely vertical motion, and wherein a plurality of said tread surfaces each has an associated vertical riser surface.

17. The system of claim 1, wherein said computer system further comprises communication components for connection to a wired or wireless network, and wherein said computer system is configured to transfer via said network a report containing data relating to treatment sessions of a patient.

18. A system comprising:
(a) a set of at least three horizontal tread surfaces;
(b) a drive system mechanically linked to said set of tread surfaces and configured to displace at least two of said tread surfaces vertically so as to adjust a rise height between adjacent of said tread surfaces in such a manner as to form a set of stairs with uniform pitch for range of different rise heights;
(c) a sensor set comprising at least one sensor deployed for measuring a parameter related to physiotherapy performed using said set of stairs; and
(d) a computer system comprising at least one processor and a non-volatile data storage medium, said computer system being associated with said sensor set so as to receive said at least one parameter,
wherein said at least one sensor comprises at least one load cell de loved to measure a load applied to each of said tread surfaces, and wherein said computer system is configured to:
(i) monitor a sum of the loads measured by said plurality of load cells; and
(ii) determine a current weight of a patient on said set of stairs,
and wherein the system further comprises a handrail extending along at least one side of said set of stairs, and wherein said computer system is further configured to subtract a current sum of said loads from said current weight to determine a current patient load on said handrail.

19. The system of claim 18, wherein said computer system is further configured to generate a warning signal if said current patient load on said handrail exceeds a predefined percentage of said current weight of the patient.

20. A system comprising:
(a) a set of at least three horizontal tread surfaces;
(b) a drive system mechanically linked to said set of tread surfaces and configured to displace at least two of said tread surfaces vertically so as to adjust a rise height between adjacent of said tread surfaces in such a manner as to form a set of stairs with uniform pitch for a range of different rise heights;
(c) a sensor set comprising at least one sensor deployed for measuring a parameter related to physiotherapy performed using said set of stairs; and
(d) a computer system comprising at least one processor and a non-volatile data storage medium, said computer system being associated with said sensor set so as to receive said at least one parameter,
wherein said at least one sensor comprises at least one load cell deployed to measure a load applied to each of said tread surfaces,
and wherein said computer system is configured to process signals from said load cells to determine a time period taken by a patient to move from one of said tread surfaces to another of said tread surfaces.

21. A system comprising:
(a) a set of at least three horizontal tread surfaces;
(b) a drive system mechanically linked to said set of tread surfaces and configured to displace at least two of said tread surfaces vertically so as to adjust a rise height between adjacent of said tread surfaces in such a manner as to form a set of stairs with uniform pitch for a range of different rise heights;
(c) a sensor set comprising at least one sensor deployed for measuring a parameter related to physiotherapy performed using said set of stairs; and
(d) a computer system comprising at least one processor and a non-volatile data storage medium, said computer system being associated with said sensor set so as to receive said at least one parameter,
wherein said at least one sensor comprises at least two load cells deployed to measure a load applied to each of said tread surfaces and to generate signals allowing determination of a loading position relative to a length of each of said tread surfaces, and wherein said computer system is configured to determine, for each stair transition by a patient, whether the patient has lead with a right leg or a left leg, and to generate an indication of bilateral or unilateral usage.

* * * * *